United States Patent [19]

Abdulla et al.

[11] 4,175,087
[45] Nov. 20, 1979

[54] α,β-UNSATURATED KETONES AND ALDEHYDES AND METHOD OF PREPARATION

[75] Inventors: Riaz F. Abdulla; Kenneth H. Fuhr, both of Greenfield, Ind.

[73] Assignee: Eli Lilly and Company, Indianapolis, Ind.

[21] Appl. No.: 868,774

[22] Filed: Jan. 12, 1978

[51] Int. Cl.$^2$ .............................................. C07C 47/45
[52] U.S. Cl. .............................. 260/586 R; 260/347.8; 260/590 C; 260/592; 260/599; 260/600 R; 549/77; 549/78; 549/70; 549/73
[58] Field of Search .................. 260/590 C, 592, 599, 260/600 R, 332.3 R, 347.8

[56] References Cited

PUBLICATIONS

Seebach et al., Tetrahedron Letters, pp. 3171–3174 (1974).

Primary Examiner—Gerald A. Schwartz
Attorney, Agent, or Firm—Dwight E. Morrison; Arthur R. Whale

[57] ABSTRACT

α,β-Unsaturated ketones and aldehydes, together with a method of preparation thereof which comprises reacting aldehydes and cyclic and acyclic ketones possessing a methyl or methylene group α- to the carbonyl function with N,N-dialkylformamide dialkyl acetal to yield the corresponding enaminoketones and enaminoaldehydes, which enaminoketones and enaminoaldehydes are allowed to react with alkyllithium reagents to yield the corresponding nitrogen-free 2-alkylidene ketones and 2-alkylidene aldehydes.

4 Claims, No Drawings

α,β-UNSATURATED KETONES AND ALDEHYDES AND METHOD OF PREPARATION

BACKGROUND OF THE INVENTION

1. Field of the Invention

The preparation of 2-alkylidene ketones and aldehydes by direct aldol condensation of an aldehyde with a ketone is usually not a practical synthetic method. Because of the value to the manufacturer of perfume intermediates, a considerable amount of research has been carried out to develop better methods of preparing the above-mentioned novel 2-alkylidene ketones and 2-alkylidene aldehydes.

2. Description of the Prior Art

In the prior art, Seebach et. al., Tetrahedron Letters, 3171–3174 (1974), describes a process for transforming ketones and aldehydes into α,β-unsaturated ketones using silylated dithiane anions and ketones.

Also in the prior art, Smith et al., J. Org. Chem., 35, 3220–3223 (1970), teach the reaction of boron difluoride complexes of 2-formylketones with organometallic reagents as constituting an effective synthesis of 2-alkylidene ketones.

Another prior art reference, Ansell et al., J. Chem. Soc., 329–331 (1959), teaches the reaction of 2-isobutoxycyclopent-2-enone with isobutyl alcohol in the presence of toluene-p-sulfonic acid to yield 2-substituted cyclopent-2-enones.

Still another prior art reference is Japanese Patent No. 51-23240 (Feb. 24, 1976), which reference claims the manufacture of 2-alkyl-2-cyclopentenone by contact of 2-alkyldienecyclopentanone with hydrogen halide or sulfonic acid.

Yet another prior art reference is Martin et al., Tetrahedron Letters, 4459–4462 (1976), which reports an allegedly facile, new procedure for the efficient preparation of a number of α-alkylidene-γ-butyrolactones starting from γ-butyrolactones and proceeding via α-n-butylthiomethylene-γ-lactones which are allowed to react with lithium dimethylcuprate or lithium di-n-butylcuprate to yield corresponding α-alkylidene-γ-lactones.

Still another reference is that of Katsin et. al., Synthetic Communications, 7 (3) 185–188 (1977), which describes a synthesis of 2-alkylcyclopent-2-en-1-ones and the corresponding cyclopentanones.

The reaction of dimethylformamide diethyl acetal with acetophenone or acetone is disclosed in Bredereck et al., Ber. 97, 3397–3406 (1964).

SUMMARY

This invention relates to novel α,β-unsaturated ketones and aldehydes and to a novel, regio specific method of preparing such α,β-unsaturated ketones and aldehydes, that is, 2-alkylidene ketones and 2-alkylidene aldehydes, by reacting enaminoketones and enaminoaldehydes with an alkyl-lithium.

DESCRIPTION OF THE PREFERRED EMBODIMENT

This invention relates to novel α,β-unsaturated ketones and aldehydes, that is, 2-alkylidene ketones and aldehydes of the formulae

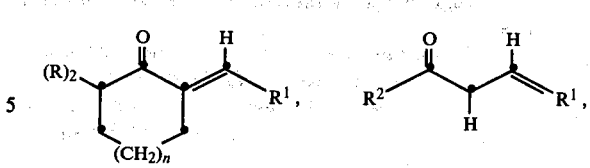

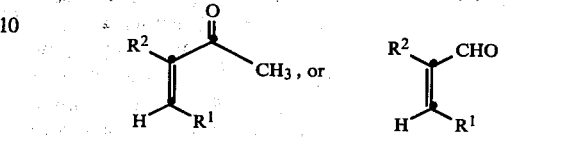

wherein
R is hydrogen or $C_1$–$C_2$ alkyl;
$R^1$ is $C_1$–$C_7$ alkyl;

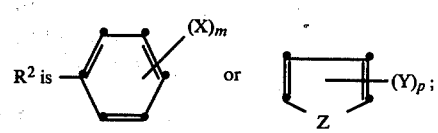

X is halo, $C_1$–$C_2$ alkyl, halo($C_1$–$C_2$)alkyl, or $C_1$–$C_2$ alkoxy;
Y is halo or $C_1$–$C_2$ alkyl;
Z is O or S;
m is 0, 1, 2, 3, 4, or 5;
n is 0, 1, 2, or 3; and
p is 0, 1 or 2.

This invention also relates to a novel method for the preparation of compounds of the formulae set forth above which comprises allowing an enaminoketone or enaminoaldehyde of the formula

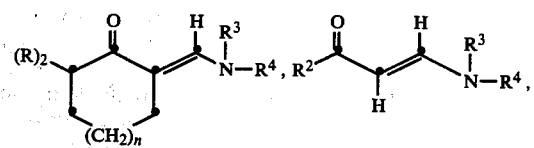

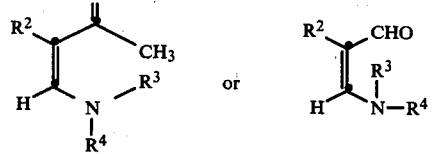

wherein R, $R^2$, and n represent the same values as above, and $R^3$ and $R^4$ are $C_1$–$C_2$ alkyl, to react with a $C_1$–$C_7$ alkyllithium ($R^1$Li) at a temperature of from about −50° to about 25° C. for a period of from about 2 to about 12 hours.

In the above formulae halo represents bromo, iodo, chloro, and fluoro.

$C_1$–$C_2$ Alkyl represents methyl or ethyl.

$C_1$–$C_2$ Alkoxy represents methoxy or ethoxy.

Halo($C_1$–$C_2$)alkyl represents trifluoromethyl, trichloromethyl, tetrafluoroethyl, pentafluoroethyl, bromo-methyl, chloromethyl, 2-chloroethyl, 2-bromoethyl, and the like.

$C_1$–$C_7$ Alkyl represents straight or branched chain saturated alkyl such as ethyl, propyl, isopropyl, n-butyl, t-butyl, sec.-butyl, n-pentyl, isopentyl, sec.-pentyl, n-hexyl, sec.-hexyl, isohexyl, n-heptyl, sec.-heptyl, isoheptyl and the like.

The novel products of this novel reaction have utility in the preparation of odorous principles of the flower oils, in particular the flower oils of several varieties of Jasminum. Others of the compounds produced by this novel reaction are usable in the preparation of some prostaglandins and furanoterpenes. As is well known, prostaglandins are important for their biological activities.

The cyclic and acyclic ketones and suitable aldehydes possessing a methyl or methylene group α- to the carbonyl function and used in preparing the enaminoketone or enaminoaldehyde starting materials, which are in turn used in the instant novel method of synthesis, are known to the art. Thus, those skilled in the art are familiar with cyclopentanone, cyclohexanone, p-chloroacetophenone, 3,4,5-trimethoxyacetophenone, benzylmethyl ketone, m-trifluoromethylbenzylmethylketone, 2,6-dimethoxyacetophenone, 3-acetyl-2,5-dimethylthiophene, phenylacetaldehyde, 3-acetylfuran, and the like.

The reaction of a cyclic or acyclic ketone or suitable aldehyde possessing a methyl or methylene group α- to the carbonyl function with an N,N-di($C_1$–$C_2$)alkylformamide di($C_1$–$C_5$)alkyl or di($C_3$–$C_6$)cycloalkyl acetal such as N,N-dimethylformamide dimethyl acetal, is carried out at the reflux temperature of the mixture under dry nitrogen gas for a time sufficient to bring about substantial completion of the reaction. Exemplary suitable acetals include but are not limited to N,N-dimethylformamide dibutyl acetal, N,N-dimethylformamide dicyclohexyl acetal, N,N-dimethylformamide diethyl acetal, N,N-dimethylformamide diisopropyl acetal, N,N-dimethylformamide dineopentyl acetal, N-ethyl-N-methylformamide diethyl acetal, N,N-diethylformamide dietyl acetal, N,N-diethylformamide dipropyl acetal, N-ethyl-N-methylformamide diethyl acetal, N,N-diethylformamide diethyl acetal, N,N-diethylformamide dipropyl acetal, N,N-dimethylformamide dicyclopropyl acetal, N,N-diethylformamide dicyclobutyl acetal, N,N-dimethylformamide dicyclopentyl acetal, and N,N-dimethylformamide dipropyl acetal, all of which named acetals are conveniently commercially available. Such reaction time ranges from about 15 hours to as long as 3 days. At the end of the reaction period, the reaction product mixture is concentrated in vacuo to dryness and the residue purified by distillation, trituration with ethyl ether, pentane, hexane, or the like, and the desired enaminoketone or enaminoaldehyde thereby isolated.

The enaminoketone or enaminoaldehyde, obtained as described supra, is then allowed to react with a $C_1$–$C_7$ alkyllithium reagent in a suitable solvent at a temperature ranging from about −50° C. to about +25° C. over a period of from about 2 to about 12 hours to produce the corresponding nitrogen-free 2-alkylidene ketone or aldehyde, also identified as α,β-unsaturated ketone or aldehyde. Suitable and desirable solvents for use in this novel process include ethers such as ethyl ether and tetrahydrofuran; hydro-carbons such as toluene, benzene, hexane, and cyclohexane; and mixtures of hydrocarbons, such mixtures being exemplified by the mixture of hexane with benzene. The preferred solvent for use in the novel process is tetrahydrofuran.

The following examples illustrate the process of this invention and the novel compounds produced thereby. As those skilled in the art will readily appreciate, other compounds can be made by using other cyclic or acyclic ketones, or suitable aldehydes, all possessing a methyl or methylene group α- to the carbonyl function, as disclosed hereinbefore.

EXAMPLE 1

2-Pentylidenecyclopentanone

To 8.4 g. (0.1 mole) of cyclopentanone was added 11.9 g. (0.1 mole) of N,N-dimethylformamide dimethyl acetal. The mixture was vigorously refluxed under dry nitrogen for about 24 hours. The reaction product mixture was then stripped dry in vacuo. There was obtained 9.45 g. of crude product. The product was identified by IR and NMR spectra and elemental analyses as 2-(N,N-dimethylaminomethylene)-cyclopentanone.

A solution of 1.39 g. (0.01 mole) of 2-(N,N-dimethylaminomethylene)cyclopentanone (synthesized above) was prepared in 100 ml. of tetrahydrofuran and the solution was cooled to −50° C. under dry nitrogen. To this solution there was added 6.5 ml. of 1.6 M n-butyllithium reagent (one equivalent). The reaction mixture was stirred during the addition, which required 5 minutes, and for one hour after the addition during which time the reaction mixture warmed to a temperature of 0° C. Thin-layer chromatography indicated that complete reaction had occurred. Two ml. of water was added to the reaction mixture after which the reaction product mixture was concentrated in vacuo, the residue was taken up in water and the aqueous mixture was extracted with ether. The ether layer was separated, washed with water, dried, and filtered. The filtrate was concentrated in vacuo to yield a yellow oil. The product was distilled and identified by IR and NMR spectra, and by elemental analyses as 2-pentylidenecyclopentanone.

Analysis calculated for: $C_{10}H_{16}O$:

|   | Theoretical | Found |
|---|---|---|
| C | 78.95 | 78.73 |
| H | 10.53 | 10.49 |

EXAMPLE 2

Trans-4'-chloro-2-heptenophenone

A mixture of 15.4 g. (0.1 mole) of p-chloroacetophenone and 15.0 g. (0.13 mole) of dimethylformamide dimethyl acetal was refluxed for about 15 hours under nitrogen. The reaction product mixture was concentrated in vacuo to leave an orange residue which was triturated in cold ether and filtered. The material so obtained was recrystallized from ether to yield 18 g. (85%) of product having a melting point of about 86°–87° C. It was identified by elemental analyses as trans 4'-chloro-3-(dimethylamino)acrylophenone.

Analysis calculated for: $C_{11}H_{12}ClNO$:

|   | Theoretical | Found |
|---|---|---|
| C | 63.01 | 62.87 |
| H | 5.77 | 5.55 |

-continued

| | Theoretical | Found |
|---|---|---|
| N | 6.68 | 6.41 |

To 2.09 g. (0.01 mole) of trans 4'-chloro-3-(dimethylamino)acrylophenone in 75 ml. of anhydrous tetrahydrofuran cooled to −30° C., there was added dropwise an equivalent amount of n-butyllithium (6.3 ml. of a 1.6 M solution). The reaction mixture was stirred overnight under nitrogen. At the end of that time, 20 ml. of water was added cautiously and the mixture was concentrated in vacuo. The oily residue was dissolved in methylene dichloride, washed with water, and dried over anhydrous magnesium sulfate. The drying agent was filtered off and the filtrate was concentrated in vacuo. The residue was chromatographed on silica gel using benzene as the solvent and the eluent. The eluate was concentrated and the residue was distilled by microdistillation to yield 1.5 g. (68%) of product having an $\eta_D^{25}$ 1.5469, and identified by elemental analyses as trans 4'-chloro-2-heptenophenone.

Analysis calculated for $C_{13}H_{15}ClO$:

| | Theoretical | Found |
|---|---|---|
| C | 70.11 | 69.85 |
| H | 6.79 | 6.54 |

EXAMPLE 3

1-(3,4,5-Trimethoxyphenyl)-2-hepten-1-one

A mixture of 21.0 g. (0.1 mole) of 3,4,5-trimethoxyacetophenone and 15.0 g. (0.13 mole) of dimethylformamide dimethyl acetal was refluxed for about 15 hours. The reaction mixture was concentrated in vacuo and the orange residue was triturated with ether and filtered. The yellowish-orange solid thus obtained was recrystallized from a mixture of benzene and hexane to yield 23.0 g. (88.5%) of product having a melting point of 125°-126° C. and identified by elemental analyses as 3-(dimethylamino)-3',4',5'-trimethoxyacrylophenone.

Analysis calculated for $C_{14}H_{19}NO_4$:

| | Theoretical | Found |
|---|---|---|
| C | 63.38 | 63.21 |
| H | 7.22 | 7.04 |
| N | 5.28 | 5.10 |

To 6.3 g. (0.03 mole) of 3-(dimethylamino)-3',4',5'-trimethoxyacrylophenone in 100 ml. of anhydrous tetrahydrofuran cooled to −30° C. under nitrogen was added dropwise 18.6 ml. of a 1.63 M solution of n-butyllithium in hexane. The mixture was allowed to warm to room temperature and was stirred overnight. The reaction mixture was worked up by adding 20 ml. of water and concentrating the mixture in vacuo. The oily residue was taken up in ether and washed successively with water and saturated aqueous sodium chloride, and dried over anhydrous magnesium sulfate. The drying agent was filtered off and the filtrate was concentrated in vacuo. The dark oil which remained was chromatographed on silica gel using benzene as the solvent and eluent. The fractions which were collected were concentrated in vacuo to yield a yellow oil which was purified by molecular distillation to yield 5.0 g. (60%) of product having a $\eta_D^{25} = 1.5473$, and identified by elemental analyses as 1-(3,4,5-trimethoxyphenyl)-2-hepten-1-one.

Analysis calculated for: $C_{16}H_{22}O_4$:

| | Theoretical | Found |
|---|---|---|
| C | 69.04 | 69.29 |
| H | 7.97 | 7.92 |

EXAMPLE 4

2-Pentylidenecyclohexanone

A mixture of 9.8 g. (0.1 mole) of cyclohexanone and 11.9 g. (0.1 mole) of dimethylformamide dimethyl acetal was refluxed overnight. The reaction product mixture was concentrated in vacuo and the residual oil was distilled in a Kugelrohr oven. An NMR spectrum of the distillate showed mainly the desired material identified as 2-(N,N-dimethyl-aminomethylene) cyclohexanone. The yield was 10.0 g. (66%).

To a solution prepared from 1.53 g. (0.01 mole) of 2-(N,N-dimethylaminomethylene)cyclohexanone and 100 ml. of anhydrous tetrahydrofuran maintained under an atmosphere of dry nitrogen gas and cooled to a temperature of about −30° C., there was added dropwise 4.5 ml. (0.01 mole) of a 2.3 M solution of n-butyllithium in hexane. The reaction mixture was maintained under the nitrogen atmosphere and stirring continued at −30° C. for about one-half hour, after which the reaction mixture was allowed to warm to room temperature and stirring was continued at room temperature for about 2 hours. Thin-layer chromatography showed the absence of starting material. The reaction mixture was worked up by slowly adding 10 ml. of water and the resulting mixture was concentrated in vacuo. The residue which remained was taken up in ether, washed with water, and dried over anhydrous magnesium sulfate. The drying agent was filtered off and the filtrate was concentrated in vacuo. The residue was chromatographed over silica gel using 90% benzene-10% ethyl acetate as solvent and eluent. The fractions which were collected were concentrated in vacuo and molecularly distilled to yield 1.2 g. (72.5%) of product having an $\eta_D^{25} = 1.4800$, and identified by elemental analyses as 2-pentylidenecyclohexanone.

EXAMPLE 5

1-(2,6-Dimethoxyphenyl)-2-hepten-1-one

A mixture of 2.0 g. of 6-hydroxy-2-methoxyacetophenone, 20 ml. of dimethylformamide, and 10 ml. of N,N-dimethylformamide dimethyl acetal was prepared. The mixture was heated under reflux for about 24 hours. The reaction mixture was concentrated in vacuo and the oily residue was crystallized from hexane, to yield 2.45 g. (93.8%) of a yellow powder having a melting point of about 107° C. The product was identified as 1-(2,6-dimethoxyphenyl)-3-(dimethylamino)-2-propen-1-one.

A solution of 2.35 g. of 1-(2,6-dimethoxyphenyl)-3-(dimethylamino)-2-propen-1-one in 100 ml. of anhydrous tetrahydrofuran was prepared and cooled to about −30° C. and there was added thereto 4.5 ml. of a 2.4 M solution of n-butyllithium in hexane using a syringe. After about 30 minutes at −30° C., the reaction mixture was allowed to warm to room temperature with continued stirring. There was added 50 ml. of 1 N HCl followed by 500 ml. of ether. The organic layer was separated and washed with water and dried over anhydrous magnesium sulfate. The drying agent was filtered off and the filtrate was concentrated in vacuo. The residue was purified by plate-chromatography to yield 1.56 g. (63%) of product identified as 1-(2,6-dimethoxyphenyl)-2-hepten-1-one.

EXAMPLE 6

1-(2,5-Dimethyl-3-thienyl)-2-hepten-1-one

A mixture of 5.0 g. of 3-acetyl-2,5-dimethylthiophene and 15.0 ml. of N,N-dimethylformamide dimethyl acetal was prepared and refluxed for about 3 days. The reaction product mixture was concentrated in vacuo to yield a yellow solid which was triturated under hexane and recovered by filtration. The product weighed 5.5 g. (81%) and was identified by NMR spectrum as 1-(2,5-dimethyl-3-thienyl)-3-(dimethylamino)-2-propen-1-one.

A mixture of 2.09 g. of 1-(2,5-dimethyl-3-thienyl)-3-(dimethylamino)-2-propen-1-one and 100 ml. of anhydrous tetrahydrofuran was prepared and cooled to −30° C. There was added thereto 4.5 ml. of a 2.4 M solution of n-butyllithium in hexane using a syringe. After the reaction mixture had been stirred for about 30 minutes at −30° C. the reaction was allowed to warm to room temperature and stirred for about 2 hours. The reaction mixture was worked up by adding 1 N HCl in ether. The ether layer was separated, washed with water and dried over anhydrous magnesium sulfate. The drying agent was filtered off and the filtrate was concentrated in vacuo. The residue was distilled using the Kugelrohr to yield 1.3 g. (58%) of product identified by elemental analyses as 1-(2,5-dimethyl-3-thienyl)-2-hepten-1-one.

Analysis calculated for $C_{13}H_{18}SO$:

|   | Theoretical | Found |
|---|---|---|
| C | 70.22 | 69.95 |
| H | 8.16 | 8.07 |

EXAMPLE 7

3-(α,α,α-Trifluoro-m-tolyl)-3-octen-2-one

A mixture of 20.2 g. (0.1 mole) of 1-(α,α,α-trifluoro-m-tolyl)-2-propanone and 50 ml. of N,N-dimethylformamide dimethyl acetal was refluxed for about 10 hours. The reaction mixture was then concentrated in vacuo. The remaining residue solidified on standing and was triturated several times with cold ether. The mixture was filtered and the solid which was isolated was recrystallized from a mixture of hexane and methylene dichloride to yield 20.75 g. (83%) of compound having a melting point of about 136°–137° C. and identified by elemental analyses as 4-(dimethylamino)-3-(α,α,α-trifluoro-m-tolyl)-3-buten-2-one.

Analysis calculated for $C_{13}H_{14}F_3NO$:

|   | Theoretical | Found |
|---|---|---|
| C | 60.70 | 60.86 |
| H | 5.49 | 5.77 |
| N | 5.44 | 5.21 |

A mixture was prepared of 5.14 g. (0.02 mole) of 4-(dimethylamino)-3-(α,α,α-trifluoro-m-tolyl)-3-buten-2-one and 75 ml. of dry tetrahydrofuran and there was added dropwise thereto an equivalent amount of n-butyllithium in hexane while maintaining the temperature of the reaction mixture at about −20° C. After the addition was complete the mixture was stirred for about 1 hour at a temperature of about −20° to −30° C. The reaction mixture was then allowed to warm to room temperature and 25 ml. of 1 N HCl was added and the mixture was concentrated in vacuo. The residual dark oil was taken up in 100 ml. of ether and washed with 2×50 ml. of water and dried over anhydrous magnesium sulfate. The drying agent was filtered off and the filtrate was concentrated in vacuo to give a dark oil. This oil was chromatographed over silica gel using ether as a solvent and eluent and the product was finally purified by molecular distillation. The product was identified by elemental analyses as 3-(α,α,α-trifluoro-m-tolyl)-3-octen-2-one. It weighed 4.5 g. (83% yield).

Analyses calculated for $C_{15}H_{17}F_3O$:

|   | Theoretical | Found |
|---|---|---|
| C | 66.65 | 66.46 |
| H | 6.34 | 6.04 |

EXAMPLE 8

1-(3′,4′,5′-Trimethoxyphenyl)-2-butene-1-one

A mixture was prepared of 5.3 g. (0.02 mole) of 3-(dimethylamino)-3′,4′,5′-trimethoxyacrylophenone and 100 ml. of dry tetrahydrofuran and cooled to −30° C. under an atmosphere of dry nitrogen. There was added thereto dropwise with stirring over a period of 30 minutes, 15 ml. of a 1.8 M solution of methyllithium. After the addition was complete, the cooling bath was removed and the reaction mixture stirred for about 3 hours at room temperature.

The reaction mixture was worked up by adding 10 ml. of water and then concentrating the mixture in vacuo. The residue was taken up in ether. The ether solution was washed with water and dried over anhydrous magnesium sulfate. The drying agent was filtered off and the filtrate concentrated in vacuo. The residue was chromatographed on silica gel using a solvent containing 85% hexane and 15% ethyl acetate. The eluent from the column was concentrated in vacuo to dryness. The residue was recrystallized from a mixture of hexane and acetone to yield product having a m.p. of about 69°–70° C. and identified as 1-(3′,4′,5′-trimethoxyphenyl)-2-butene-1-one. Yield 3.0 g.

Analyses calculated for $C_{13}H_{16}O_4$:

|   | Theoretical | Found |
|---|---|---|
| C | 66.09 | 66.39 |
| H | 6.83 | 7.04 |

EXAMPLE 9

α-Pentylidenebenzeneacetaldehyde

To 10 g. of phenylacetaldehyde was added 25 ml. of N,N-dimethylformamide dimethyl acetal and 50 ml. of toluene. The mixture was refluxed for about 48 hours and then concentrated to dryness in vacuo. The reaction product was chromatographed on a silica gel column using ethyl acetate as eluent. There was obtained 3.6 g. of product identified by IR and NMR spectra as N,N-dimethylatropaldehyde.

A solution of 3.5 g. of N,N-dimethylatropaldehyde, synthesized above, was prepared in 150 ml. of dry tetrahydrofuran and the solution was cooled to −30° C. under dry nitrogen. To this solution at this temperature there was added 9.0 ml. of n-butyllithium reagent over a period of two minutes. The reaction mixture was stirred and allowed to warm to room temperature over a period of about two hours. The reaction product mixture was taken up in 700 ml. of ether, the mixture washed with one portion of 1 N aqueous hydrochloric acid, dried, and concentrated in vacuo. The crude product was distilled on a Kugelrohr apparatus to yield a colorless, mobile liquid. This liquid was chromatographed on a silica gel column using chloroform as the eluent. There was obtained 0.73 g. of product identified as α-penylidenebenzeneacetaldehyde.

EXAMPLE 10

1-(3-Furanyl)-4-methyl-2-penten-1-one

A mixture of 25 g. (0.22 moles) of 3-furanoic acid and 100 g. of oxalyl chloride was refluxed for about 5 hours. The excess oxalyl chloride was removed in vacuo and the crude product purified by distillation. There was obtained 20 g. (70% yield) of product having a boiling point of about 35°–40° C./2.6 mm., identified as 3-furanoyl chloride.

To a solution of 1.9 g. (0.01 moles) of cuprous iodide (extracted with tetrahydrofuran) in 50 ml. of dry tetrahydrofuran and cooled to about −20° C., there was added 5.5 ml. of a 1.8 M solution of methyllithium (0.01 moles). The yellow solution obtained was stirred for about 20 minutes and then 1.30 g. (0.01 moles) of 3-furanoyl chloride in 10 ml. of dry tetrahydrofuran was added dropwise. The reaction mixture was stirred at about −20° C., for about 2 hours and then allowed to warm to room temperature. To the reaction product mixture there was added 25 ml. of 2 N aqueous hydrochloric acid and the mixture was then evaporated in vacuo. The semi-solid mass which remained was extracted with methylene dichloride. The methylene dichloride solution was filtered, washed with water, dried over anhydrous magnesium sulfate, and after the drying agent was filtered off the filtrate was concentrated in vacuo. There was obtained an oil which crystallized upon standing. The product weighed 1.0 g. and was identified by NMR spectrum as 3-acetylfuran. A sample recrystallized from a mixture of hexane and ethyl ether had a melting point of about 52°–54° C.

Analyses calculated for $C_6H_6O_2$:

|   | Theoretical | Found |
|---|---|---|
| C | 65.45 | 65.23 |
| H | 5.49 | 5.47 |

A mixture of 3.30 g. (0.03 moles) of 3-acetylfuran and 25 ml. of N,N-dimethylformamide dimethyl acetal was prepared and refluxed for about 12 hours. The reaction product mixture was concentrated in vacuo and the residual oil was triturated in pentane, whereupon it solidified. The solid material was recrystallized from a mixture of isopropyl ether and methylene dichloride to yield product weighing 2.9 g. (59% yield) and having a melting point of about 103°–105° C., identified as 1-(3-furanyl)-3-(dimethylamino)-2-propen-1-one.

Analyses calculated for $C_9H_{11}NO_2$:

|   | Theoretical | Found |
|---|---|---|
| C | 65.44 | 65.55 |
| H | 6.71 | 6.42 |
| N | 8.48 | 8.60 |

A mixture of 1.65 g. (0.01 moles) of 1-(3-furanyl)-3-(dimethylamino)-2-propen-1-one and 100 ml. of anhydrous tetrahydrofuran was prepared and cooled to −30° C. and there was added thereto 5.5 ml. of a 1.85 M solution of isopropyllithium in pentane. The reaction mixture was stirred for about one-half hour at −30° C. The reaction product mixture was worked up by adding 5 ml. of water and concentrating the resulting mixture in vacuo. The residue which remained was taken up in methylene dichloride, the solution washed successively with water and saturated aqueous sodium chloride solution, and dried over anhydrous magnesium sulfate. The drying agent was filtered off and the filtrate concentrated in vacuo. The material which remained was chromatographed on silica gel using methylene dichloride and then 95% methylene dichloride-5% ethyl acetate as eluent. The first product off the column was the desired material, the yield of which was 600 mg. and was identified by NMR spectrum as 1-(3-furanyl)-4-methyl-2-penten-1-one. The structure of this product was further established by hydrogenation of the 1-(3-furanyl)-4-methyl-2-penten-1-one in ethanol and over 5% palladium on carbon to yield perillaketone, a naturally-occurring furanoterpene originally isolated from *Perilla frutescens* Brit. by Goto, *J. Pharm. Soc.* Japan, 57, 77 (1937).

We claim:

1. A process for preparing 2-alkylidene ketones of the formula

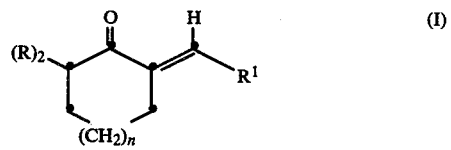

wherein
R is hydrogen or $C_1$–$C_2$ alkyl;
$R^1$ is $C_1$–$C_7$ alkyl; and
n is 0 or 1,
which comprises allowing an enaminoketone of the formula

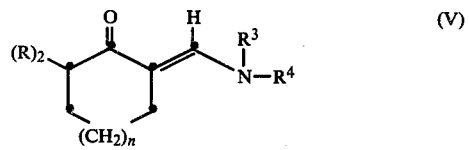

wherein R and n represent the same values as above, and $R^3$ and $R^4$ are $C_1$–$C_2$ alkyl, to react with a $C_1$–$C_7$ alkyllithium in the presence of a solvent at a temperature of from about −50° to about 25° C. for a period of from about 2 to about 12 hours.

2. The process of claim 1 wherein the solvent is tetrahydrofuran.

3. A process as in claim 1 wherein the product is 2-pentylidenecyclopentanone.

4. A process as in claim 1 wherein the product is 2-pentylidenecyclohexanone.

* * * * *